United States Patent [19]

Seipler et al.

[11] Patent Number: 5,418,465
[45] Date of Patent: May 23, 1995

[54] MEASURING CELL FOR USE WITH A SENSOR FOR MEASURING THE MIXTURE RATIO OF LIQUIDS

[75] Inventors: Dieter Seipler; Botho Ziegenbein; Bernd Maihoeffer, all of Reutlingen, Germany

[73] Assignee: Robert Bosch GmbH, Germany

[21] Appl. No.: 50,057

[22] PCT Filed: Oct. 10, 1991

[86] PCT No.: PCT/DE91/00798

§ 371 Date: Jun. 22, 1993

§ 102(e) Date: Jun. 22, 1993

[87] PCT Pub. No.: WO92/08126

PCT Pub. Date: May 14, 1992

[30] Foreign Application Priority Data

Oct. 30, 1990 [DE] Germany .............. 40 34 471.1

[51] Int. Cl.$^6$ .............. G01R 27/26; G01N 27/22
[52] U.S. Cl. .............. 324/663; 324/71.1;
  324/664; 324/686; 324/690; 73/61.43
[58] Field of Search .............. 324/658, 663, 664, 670,
  324/672, 685, 686, 690, 71.1; 73/61.41, 61.43,
  861.08, 861.12

[56] References Cited

U.S. PATENT DOCUMENTS

| | | | |
|---|---|---|---|
| 4,470,300 | 9/1984 | Kobayashi | 73/61.43 X |
| 4,484,582 | 11/1984 | Rottenberg et al. | 73/861.08 X |
| 4,710,757 | 12/1987 | Haase | 324/663 X |
| 4,905,655 | 3/1990 | Maekawa | 123/494 |
| 5,151,660 | 9/1992 | Powers et al. | 324/663 X |

FOREIGN PATENT DOCUMENTS

| | | |
|---|---|---|
| 0280229 | 8/1988 | European Pat. Off. . |
| 0291363 | 11/1988 | European Pat. Off. . |
| 3843097 | 7/1989 | Germany . |
| 57-57253 | 7/1982 | Japan . |
| 63-67556 | 8/1988 | Japan . |

*Primary Examiner*—Kenneth A. Wieder
*Assistant Examiner*—Diep Do
*Attorney, Agent, or Firm*—Kenyon & Kenyon

[57] ABSTRACT

A sensor for measuring the mixture ratio of liquids, particularly of fuel mixtures, comprises a measuring cell, which has a cavity with one inlet and one outlet. The liquid is directed through the cavity, whereby regions of the inner wall of the cavity are electrically conductive and, together with at least one additional electrically conductive surface, form a capacitor, which is a component of an evaluation circuit. The measuring cell is manufactured from at least two ceramic carriers, which are connected by way of at least one connection layer to form a layer arrangement. The cavity is produced between the ceramic carriers as the result of the lack of at least one connection layer in certain regions. In each case, at least one electrode is applied, in the vicinity of the cavity, to the ceramic carrier delimiting the cavity using thick-film technology.

23 Claims, 1 Drawing Sheet

1

MEASURING CELL FOR USE WITH A SENSOR FOR MEASURING THE MIXTURE RATIO OF LIQUIDS

FIELD OF THE INVENTION

The present invention relates to a sensor for measuring the mixture ratio of liquids and in particular to a small-scale sensor for measuring the mixture ratio of fuel mixtures.

BACKGROUND OF THE INVENTION

European Patent Application No. 0 335 168 A2 describes a sensor which determines the alcoholic concentration of a fuel mixture to allow an internal combustion engine to be optimally operated. The sensor's measuring cell has an inlet and an outlet to allow the fuel mixture to flow through the measuring cell. The outer walls of the measuring cell and a central cylinder consist, at least partially, of conductive material and form a cylindrical capacitor, which is a component of an evaluation circuit. The capacitance of the cylindrical capacitor is influenced by the composition of the fuel mixture which constitutes the dielectric. Not only does the capacitance change along with the composition, but the conductance of the fuel mixture changes as well. This conductance is likewise detected by means of the capacitor's electrodes. Up until now, this arrangement had been realized in macroscopic dimensions using conventional manufacturing methods.

SUMMARY OF THE INVENTION

The present invention provides a sensor for measuring the mixture ratio of liquids, in which first and second electrodes are applied to first and second ceramic carriers, respectively. At least one of the first and second electrodes is applied using thick-film technology. The first and second ceramic carriers define a cavity therebetween for carrying the liquids.

An advantage of the sensor according to the present invention is that it is able to be realized on a very small scale, so that its application does not require any significant amount of additional space. It is also advantageous that the ceramic housing of the measuring cell demonstrates very good media compatibility, particularly for fuel mixtures. Furthermore, it is advantageous that the sensor is able to be assembled using known methods that are easily mastered, and using materials from thick-film technology. The housing can be manufactured and the circuit elements, such as the electrodes of the measuring capacitor, can be applied in one process step.

It is particularly advantageous for the measuring cell to have another sealed cavity, on whose inner walls electrodes are applied. Together with a reference medium filling the additional cavity, these electrodes form a reference capacitor, which likewise constitutes a component of the evaluation circuit. Long-term drifts and the temperature sensitivity of the sensor can be reduced by incorporating a reference capacitor in the measuring process. This is because, given the same operating conditions, the characteristic of the reference capacitor changes similarly to the characteristic of the first capacitor, whose dielectric is the liquid to be measured.

Since the reference medium is supposed to be occluded in the additional cavity, but is subject to thermal expansion, it is advantageous for the additional cavity to communicate via a passage with a compensating volume. One advantageous refinement of the compensating volume, which is likewise filled with the reference medium, consists in developing one boundary wall of the compensating volume as a flexible ceramic membrane. Another advantageous method for compensating for the temperature sensitivity of the sensor consists in measuring the temperature of the liquid or of the reference medium directly. This can be achieved advantageously by applying temperature-dependent resistors, using thick-film technology, to the inner walls of a cavity or of the compensating wall, to place them in direct contact with the liquid or with the reference medium. The structure of the measuring cell in thick-film technology makes it possible for parts of or for the entire evaluation circuit to be applied to the measuring cell itself using thick-film hybrid technology. This increases the interference immunity of the signal evaluation. Furthermore, the measuring cell structure makes it possible to use inexpensive ceramic molded components, in which the inlet and the outlet of the measuring cell have already been formed.

The cavities of the measuring cell are formed by the absence of the connection layer in certain regions. Particularly suited as a connection layer in this context is a glass layer, which is able to be applied, in the form of a simply structured thick-film paste, to a ceramic carrier. Such a glass layer makes it possible to establish a connection to another ceramic carrier during vitrification. This method is well-known and has been adequately developed.

BRIEF DESCRIPTION OF THE DRAWINGS

FIG. 1b is a cross-sectional view of the sensor shown in FIG. 1a.

DETAILED DESCRIPTION

Figure 1A:
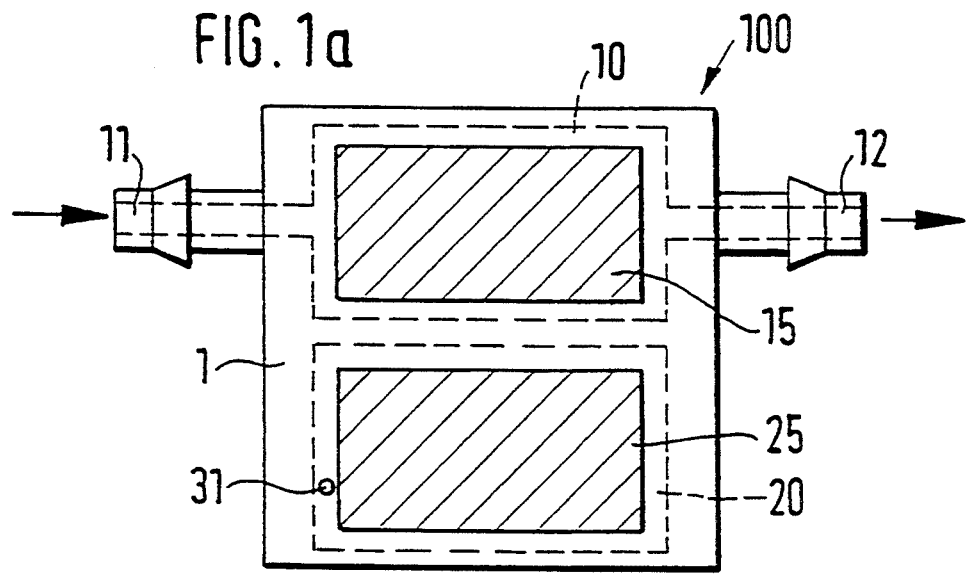
FIG. 1a is a top plan view of a first embodiment of the sensor according to the present invention.
Figure 1B:
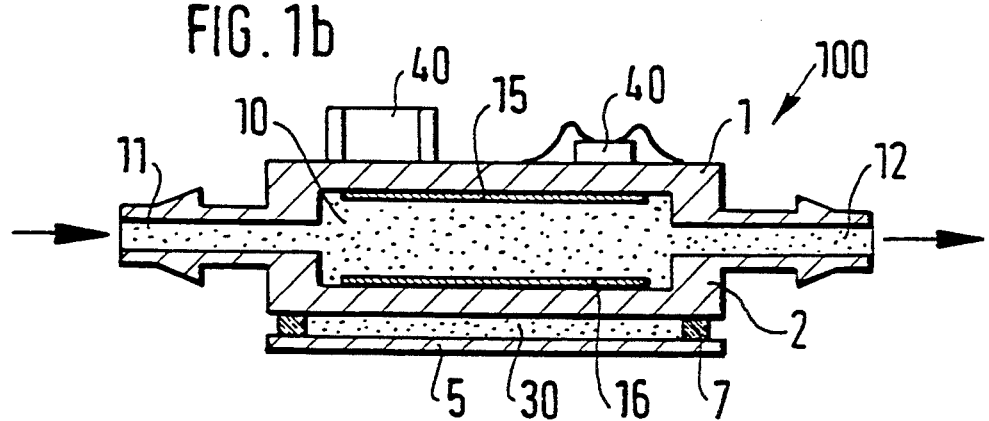

In FIGS. 1a and 1b, 100 designates a measuring cell, which is manufactured from ceramic carriers 1 and 2 developed as ceramic molded components. The ceramic molded component 1 forms an upper cover, in which the top sides of an inlet 11 and of an outlet 12 have already been formed. The ceramic molded component 2 constitutes the mating component, which serves as the bottom side of the measuring cell. The two ceramic molded components 1 and 2 are interconnected by a connection layer, which cannot be seen in the views depicted in FIG. 1. Two distinct cavities 10 and 20, formed by the lack of the connection layer in certain regions, are situated inside the measuring cell 100. A liquid, whose mixture ratio is supposed to be determined, can be directed via the inlet 11 and the outlet 12 through the measuring cell 100, whereby the liquid traverses only the one cavity 10. The direction of flow is indicated by the arrows. Electrodes 15 and 16 are applied, respectively, to two diametrically opposing inner walls of the cavity 10, which are formed from the ceramic carriers 1, 2. As depicted in FIG. 1b, the two electrodes 15 and 16 constitute a plate capacitor having the traversing liquid as a dielectric, whose capacitance fluctuates depending on the mixture ratio of the liquid.

This measuring capacitor is part of an evaluation circuit, denoted in FIG. 1b by 40, which is applied, in part, directly to the measuring cell using thick-film hybrid technology. As in the first cavity 10, two electrodes are applied to two diametrically opposing inner walls of another cavity 20. Of these, only one electrode 25 is depicted in FIG. 1a, since the second cavity 20 is arranged next to the first cavity 10, so that the boundary walls of the first cavity 10 and of the second cavity 20 are formed by the same ceramic carriers 1 and 2. A reference medium is contained in the second cavity 20 and serves as a dielectric for the reference capacitor formed by the electrodes in the second cavity 20. This reference capacitor is likewise a component of the evaluation circuit 40. One is able to use this reference capacitor to compensate, on the one hand, for the temperature sensitivity of the sensor and, on the other hand, for long-term drifts in the characteristic, since the operating conditions of the measuring capacitor and of the reference capacitor largely conform and it is, therefore, expected that their characteristics change in the same manner over time.

In FIG. 1a, 31 denotes a passage. This passage 31 consists of a bore hole in the ceramic carrier 2 in the vicinity of the cavity 20. It establishes a connection between the cavity 20 and a compensating volume 30, which is likewise filled with the reference medium. The compensating volume 30 is a cavity disposed between the ceramic carrier 2 and a flexible ceramic membrane 5, which is applied over an intermediate layer 7 to the ceramic carrier 2. This ceramic membrane 5 renders possible, for example, a temperature-induced volume change in the reference medium, which completely fills the second cavity 20 and the compensating volume 30.

Circuit elements, such as resistors and electrodes of capacitors, are able to be printed very simply, using screen printing technology, onto the ceramic substrate of the measuring cell 100. For this purpose, steel or polyester screens are prepared in such a way that their mesh apertures are open for the places to be printed and are closed in-between. Using a doctor blade, a suitable paste is forced through the screen and spread onto the ceramic substrate. It can also be that several printing steps are required, in which different pastes are used. After the printing, the paste is dried at a somewhat elevated temperature, and subsequently fired. The ceramic carriers are also connected using this method. A structured glass layer is preferably used as a connection layer. Besides the electrodes, it is also advantageous to print temperature-dependent resistors inside the cavities 10 and 20, or also in the compensating volume 30, in order to detect the temperature of the liquid and/or of the reference medium.

Figure 2:
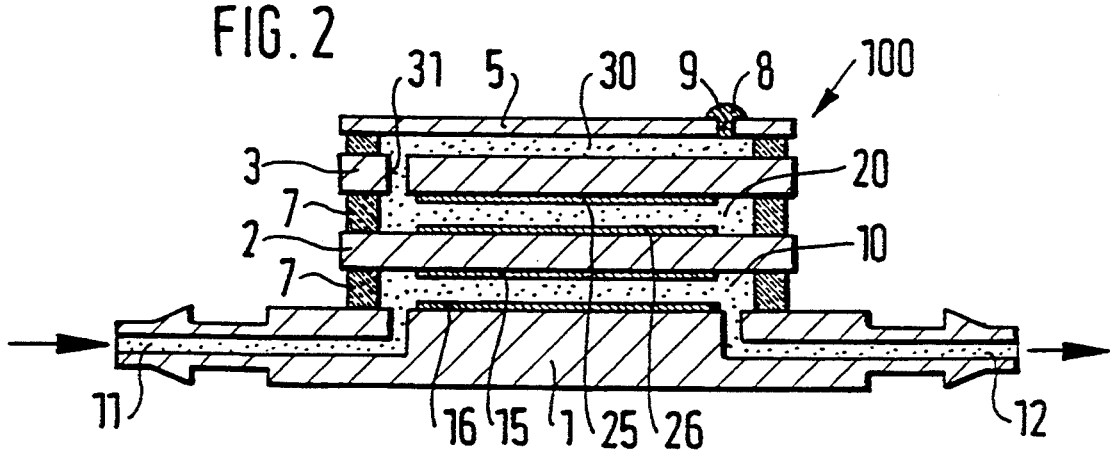
FIG. 2 is a cross-sectional view of a second embodiment of the sensor according to the present invention.

FIG. 2 depicts a measuring cell 100, in which two cavities 10 and 20 are arranged, one over the other. The measuring cell 100 in this example is formed by glazing three ceramic carriers 1, 2 and 3 onto one another and onto one ceramic membrane 5. The ceramic carrier 1 is a ceramic molded component, in which an inlet 11 and an outlet 12 are formed. The cavity 10 is designed as an interstitial space between the ceramic carriers 1 and 2. Electrodes 15 and 16 are applied to the ceramic carriers 1 and 2 in the vicinity of the cavity 10. Furthermore, the cavity 10 communicates with the inlet 11 and the outlet 12 formed in the ceramic carrier 1, so that the liquid, whose mixture ratio is supposed to be determined, constitutes the dielectric of the capacitor arranged in the cavity 10.

A reference medium is occluded in the second cavity 20 between the ceramic carriers 2 and 3, in which, likewise, two electrodes 25 and 26 form a reference capacitor. The cavity 20 communicates via a bore hole 31 with a compensating volume 30, which is delimited by a flexible ceramic membrane 5. The cavity 20 and the compensating volume 30 are manufactured in the same manner as the cavity 10 with the help of connection layers 7. The side walls are formed in each case by the structured glass-connection layers 7. Situated in the ceramic membrane 5 is a bore hole 9, through which the reference medium is poured into the cavity 20 and into the compensating volume 30. As a seal 8 for the bore hole 9, one can advantageously use a solder drop, which is applied to the metal-plated bore hole 9. FIG. 2 dispenses with portraying an evaluation circuit. The method of functioning of the sensor depicted in FIG. 2 corresponds to that of the sensor shown in FIG. 1a and 1b.

I claim:

1. A cell for measuring a mixture ratio of a liquid, comprising:
    a first elongated member;
    a second elongated member coupled opposite of, and adjacent to, the first elongated member, the first and second elongated members defining a passage therebetween, the passage having an inlet for receiving the liquid and an outlet for releasing the liquid;
    a first electrode coupled to the first elongated member adjacent to the passage;
    a second electrode coupled to the second elongated member adjacent to the passage; and
    at least one connection layer arranged between the first elongated member and the second elongated member for coupling the first and second elongated members, the connection layer and the first and second elongated members defining the passage, the connection layer being composed of glass and being structured using a thick-film technique,
    wherein at least one of the first and second electrodes is applied to a corresponding at least one of the first and second elongated members using the thick-film technique.

2. The cell according to claim 1, wherein the liquid is a fuel mixture.

3. The cell according to claim 1, wherein the first and second elongated members are ceramic molded.

4. The cell according to claim 1, further comprising at least one connection layer arranged between said first elongated member and said second elongated member for coupling the first and second elongated members, the connection layer and the first and second elongated members defining the passage, the connection layer being composed of glass and being structured using the thick-film technique.

5. The cell according to claim 1, wherein the first and second electrodes form a capacitor, the capacitor being electrically coupled to an evaluation circuit.

6. The cell according to claim 5, wherein at least a portion of the evaluation circuit is applied to said first elongated member using the thick-film technique.

7. The cell according to claim 5, further comprising:
    a third elongated member physically coupled adjacent to the second elongated member through an intermediate connection layer, the second and third elongated members defining an additional passage therebetween;
    a third electrode coupled to the second elongated member adjacent to the additional passage;
    a fourth electrode coupled to the third elongated member adjacent to the additional passage;

wherein at least one of the third and fourth electrodes is applied to a corresponding at least one of the second and third elongated members using the thick-film technique.

8. The cell according to claim 7, wherein:
the additional passage is filled with a reference medium;
the reference medium and the third and fourth electrodes form an additional capacitor; and
the additional capacitor is electrically coupled to the evaluation circuit.

9. The cell according to claim 8, further comprising a membrane coupled adjacent to the third elongated member through a second intermediate connection layer thereby defining a compensating volume in fluid communication with the additional passage.

10. The cell according to claim 9, wherein the membrane is a flexible ceramic membrane.

11. The cell according to claim 9, wherein the membrane has a bore hole for introducing the reference medium into the additional passage, the bore hole being sealed after the reference medium is introduced.

12. The cell of claim 1 wherein the first elongated member and second elongated member further define a cavity, the cavity being isolated from the passage, the cell further comprising:
a third electrode coupled to the first elongated member adjacent to the cavity;
a fourth electrode coupled to the second elongated member adjacent to the cavity; and
a reference medium contained in the cavity,
wherein the third electrode and the fourth electrode form a reference capacitor, and
wherein the reference medium serves as a dielectric for the reference capacitor.

13. The cell of claim 12 wherein the first electrode and the second electrode form a measuring capacitor, and further comprising:
an evaluation circuit, the evaluation circuit being electrically coupled with the first electrode, the second electrode, the third electrode, and the fourth electrode,
wherein the evaluation circuit uses the reference capacitor to compensate for temperature sensitivity of the measuring capacitor and for long term drifts in a characteristic of the measuring capacitor.

14. A cell for measuring a mixture ratio of a liquid comprising:
a) a first carrier;
b) a second carrier physically coupled to the first carrier thereby defining a cavity for containing the liquid, an inlet for receiving the liquid, and an outlet for releasing the liquid;
c) a first electrode formed on the first carrier on an inside surface of the cavity such that it can be in direct contact with liquid contained in the cavity; and
d) a second electrode formed on the second carrier on an inside surface of the cavity such that it can be in direct contact with the liquid contained in the cavity.

15. The cell of claim 14 wherein the first carrier is a ceramic material and the second carrier is a ceramic material.

16. The cell of claim 14 wherein at least one of said first carrier and said second carrier includes a recess which defines an additional cavity, said additional cavity being isolated from the cavity and containing a reference liquid.

17. The cell of claim 16 further comprising:

a third electrode formed on the first carrier on an inside surface of the additional cavity; and
a fourth electrode formed on the second carrier on an inside surface of the additional cavity.

18. The cell of claim 16 further comprising:
a flexible membrane;
an intermediate layer, the intermediate layer disposed between, and physically coupling, the second carrier and the flexible membrane thereby defining a compensating volume,
wherein the second carrier includes a bore hole in an area of the additional cavity such that the additional cavity is in fluid communication with the compensating volume.

19. A sensor cell for measuring a mixture ratio of a liquid, comprising:
(a) a first elongated member;
(b) a second elongated member coupled opposite of, and adjacent to, the first elongated member, the first and second elongated members defining a passage therebetween, the passage having an inlet for receiving the liquid and an outlet for releasing the liquid;
(c) a first electrode coupled to the first elongated member adjacent to the passage;
(d) a second electrode coupled to the second elongated member adjacent to the passage;
(e) a third electrode in a cavity, the cavity being adjacent to the second elongated member;
(f) a fourth electrode in the cavity;
(g) a reference medium contained in the cavity; and
(h) an evaluation circuit, the evaluation circuit being electrically coupled with the first electrode, the second electrode, the third electrode, and the fourth electrode,
wherein at least one of the first and second electrodes is applied to a corresponding at least one of the first and second elongated members using a thick-film technique,
wherein the first and second electrodes form a measuring capacitor,
wherein the third electrode and the fourth electrode form a reference capacitor,
wherein the reference medium serves as a dielectric for the reference capacitor, and
wherein the evaluation circuit uses the reference capacitor to compensate a signal of the measuring capacitor.

20. The cell according to claim 19, further comprising:
a third elongated member physically coupled to the second elongated member, the second and third elongated members defining the cavity therebetween,
wherein the third electrode is coupled to the second elongated member adjacent to the cavity and the fourth electrode is coupled to the third elongated member adjacent to the cavity, and
wherein at least one of the third and fourth electrodes is applied to a corresponding at least one of the second and third elongated members using the thick-film technique.

21. The cell according to claim 20, further comprising a membrane coupled to the third elongated member thereby defining a compensating volume in fluid communication with the cavity.

22. The cell according to claim 21, wherein the membrane is a flexible ceramic membrane.

23. The cell according to claim 21, wherein the membrane has a bore hole for introducing the reference medium into the cavity, the bore hole being sealed after the reference medium is introduced.

* * * * *